(12) United States Patent
Nie

(10) Patent No.: US 11,963,804 B2
(45) Date of Patent: Apr. 23, 2024

(54) ANTI-COLLISION APPARATUS AND RADIOTHERAPY DEVICE

(71) Applicant: OUR UNITED CORPORATION, Xi'an (CN)

(72) Inventor: Ziheng Nie, Xi'an (CN)

(73) Assignee: OUR UNITED CORPORATION, Xi'an (CN)

( * ) Notice: Subject to any disclaimer, the term of this patent is extended or adjusted under 35 U.S.C. 154(b) by 262 days.

(21) Appl. No.: 17/609,910

(22) PCT Filed: Jun. 4, 2020

(86) PCT No.: PCT/CN2020/094465
§ 371 (c)(1),
(2) Date: Nov. 9, 2021

(87) PCT Pub. No.: WO2021/051891
PCT Pub. Date: Mar. 25, 2021

(65) Prior Publication Data
US 2022/0202379 A1  Jun. 30, 2022

(30) Foreign Application Priority Data

Sep. 20, 2019  (CN) .......................... 201910895139.X
Sep. 20, 2019  (CN) .......................... 201921580260.5

(51) Int. Cl.
*A61B 6/10* (2006.01)
*A61N 5/10* (2006.01)

(52) U.S. Cl.
CPC ................ *A61B 6/102* (2013.01); *A61N 5/10* (2013.01)

(58) Field of Classification Search
None
See application file for complete search history.

(56) References Cited

U.S. PATENT DOCUMENTS 3,308,903 A * 3/1967 Sobel ...................... B60R 19/44
200/61.44
4,539,880 A * 9/1985 Barber ..................... B26D 3/10
83/468.8

(Continued)

FOREIGN PATENT DOCUMENTS

| CN | 204745370 U | 11/2015 |
| CN | 206183817 U | 5/2017 |

(Continued)

OTHER PUBLICATIONS

International Search Report and Written Opinion issued in corresponding International Patent Application No. PCT/CN2020/094465 dated Aug. 27, 2020, with English translation.

*Primary Examiner* — Hoon K Song
(74) *Attorney, Agent, or Firm* — Morgan, Lewis & Bockius LLP

(57) ABSTRACT

An anti-collision apparatus comprises an anti-collision cover and a detection portion. The detection portion is provided outside the bottom end of the anti-collision cover along the axial direction of the anti-collision cover, and an axial clearance is provided between the detection portion and the anti-collision cover. The detection portion is configured to collect a trigger signal and output a collision signal according to the trigger signal; the trigger signal comprises a mechanical trigger signal or an electromagnetic trigger signal generated in the case that the axial clearance is reduced to a target value.

13 Claims, 4 Drawing Sheets

(56) References Cited

U.S. PATENT DOCUMENTS

| | | | | |
|---|---|---|---|---|
| 4,969,170 | A | * 11/1990 | Kikuchi | .................. A61N 5/10 |
| | | | | 378/114 |
| 10,272,265 | B2 | 4/2019 | Filiberti et al. | |
| 2018/0031441 | A1* | 2/2018 | Wong | ..................... H01H 13/28 |
| 2019/0316647 | A1* | 10/2019 | Endler | ..................... F16F 3/10 |

FOREIGN PATENT DOCUMENTS

| | | |
|---|---|---|
| CN | 208990086 U | 6/2019 |
| CN | 109966659 A | 7/2019 |
| CN | 209154912 U | 7/2019 |
| CN | 210844992 U | 6/2020 |

\* cited by examiner

ANTI-COLLISION APPARATUS AND RADIOTHERAPY DEVICE

CROSS-REFERENCE TO RELATED APPLICATIONS

This application is a national phase entry under 35 USC 371 of International Patent Application NO. PCT/CN2020/094465 filed on Jun. 4, 2020, which claims priority to Chinese Patent Application No. 201910895139.X and No. 201921580260.5, filed on Sep. 20, 2019, which are incorporated herein by reference in their entirety.

TECHNICAL FIELD

The present disclosure relates to the technical field of medical equipment, and in particular, to an anti-collision apparatus and a radiotherapy device.

BACKGROUND

Radiotherapy, chemotherapy and surgery are three common methods in the current cancer therapy process. Approximately 70% of cancer patients require radiation therapy in the process of cancer therapy. Approximately 40% of cancers may be radical cured by radiation therapy. Radiotherapy devices are generally divided into two types: head tumor radiotherapy devices and body tumor radiotherapy devices. The head tumor radiotherapy devices mostly use a rotatable collimating body with a hemispherical cavity or a truncated conical cavity as an irradiation therapy cavity.

SUMMARY

In one aspect, an anti-collision apparatus is provided. The anti-collision apparatus includes an anti-collision cover and a detection component. The detection component is disposed outside a bottom end of the anti-collision cover along an axial direction of the anti-collision cover, and an axial gap is provided between the detection component and the anti-collision cover. The detection component is configured to collect a trigger signal and to output a collision signal according to the trigger signal; the trigger signal includes a mechanical trigger signal or an electromagnetic trigger signal generated when the axial gap is reduced to a target value.

In another aspect, a radiotherapy device is provided. The radiotherapy device includes: a device body, a collimating body and the anti-collision apparatus as described above. The collimating body is rotatably connected to the device body. The anti-collision apparatus is located inside the collimating body and is fixedly connected to the device body.

BRIEF DESCRIPTION OF THE DRAWINGS

In order to describe technical solutions in some embodiments of the present disclosure more clearly, the accompanying drawings to be used in the description of some embodiments will be briefly described below. Obviously, the accompanying drawings to be described below are merely accompanying drawings of some embodiments of the present disclosure, and a person of ordinary skill in the art may obtain other drawings according to these drawings.

DETAILED DESCRIPTION

Figure 1:
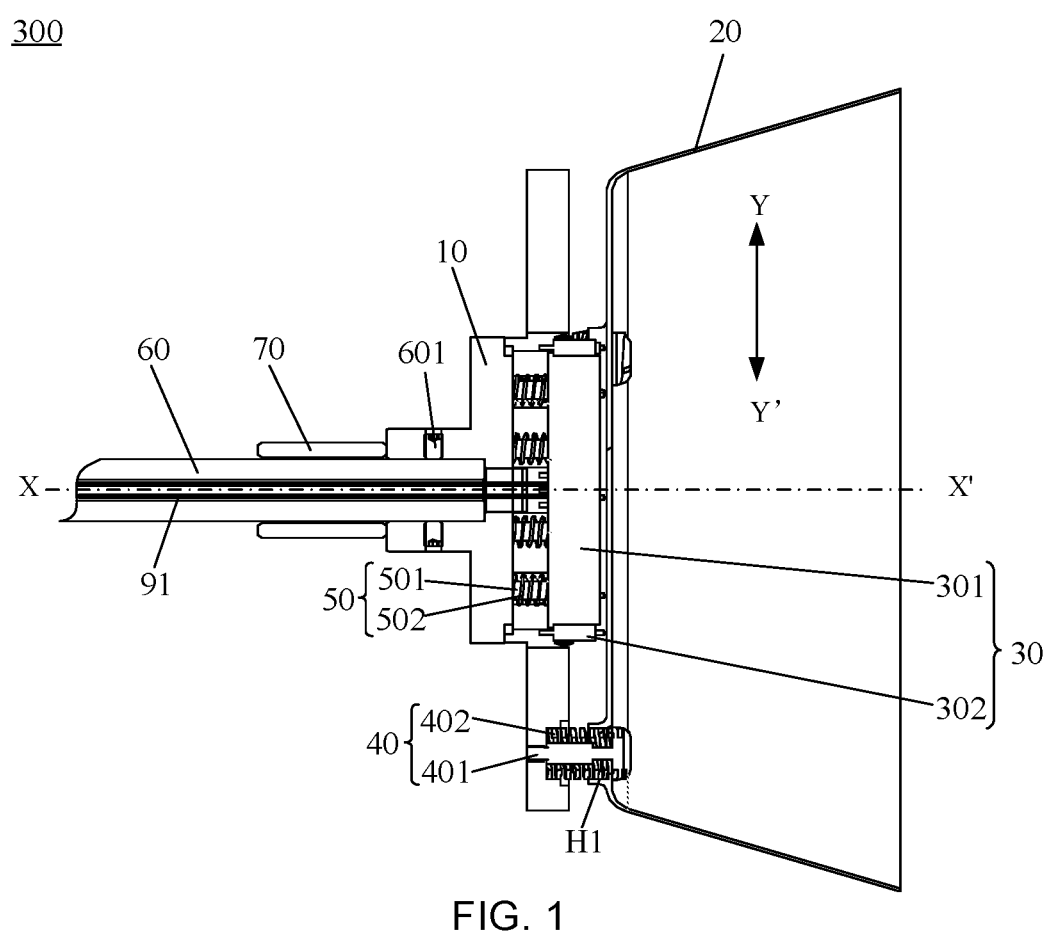
FIG. 1 is a schematic sectional view of an anti-collision apparatus, in accordance with some embodiments of the present disclosure.

Technical solutions in the embodiments of the present disclosure will be described clearly and completely with reference to the accompanying drawings in some embodiments of the present disclosure. Obviously, the described embodiments are merely some but not all embodiments of the present disclosure. All other embodiments obtained by a person of ordinary skill in the art on the basis of some embodiments of the present disclosure shall be included in the protection scope of the present disclosure.

In the description of some embodiments of the present disclosure, it will be understood that orientations and positional relationships indicated by terms "center," "upper," "lower," "front," "back," "left," "right," "vertical," "horizontal," "top," "bottom," "inner," "outer," and the like are based on the orientations and positional relationships indicated in the drawings. The orientations and positional relationships are merely to facilitate the description of some embodiments of the present disclosure and to simplify the description, and are not intended to indicate or imply that the referenced devices or elements must have a particular orientation, be constructed and operated in a particular orientation, and therefore are not to be construed as limiting the present disclosure.

Terms such as "first" and "second" are only used for descriptive purposes, and are not to be construed as indicating or implying the relative importance or implicitly indicating the number of indicated technical features. Thus, features defined with "first" or "second" may explicitly or implicitly include one or more of the features. In the description of some embodiments of the present disclosure, the term "a plurality of/the plurality of" means two or more unless otherwise specified.

In the description of the present disclosure, it will be noted that the term "mounted", "communicated" or "connected" should be understood broadly unless specifically stated or defined otherwise. For example, it may be a fixed connection, a detachable connection, or an integral connection; it may be a mechanical connection or an electrical connection; and it may be a direct connection, or may be an indirect connection through an intermediate medium, or may be an internal communication between two elements. Specific meanings of the above terms in some embodiments of the present disclosure will be understood by those of ordinary skill in the art as the case may be.

In the related art, a head tumor radiotherapy device is used to perform radiation therapy on a patient with a lesion in the head. During the treatment of the radiation therapy to the patient, the patient is lying on the back on a three-dimensional therapy couch, and the patient's head is fixed by the head frame positioning apparatus. In this way, the three-dimensional therapy couch is controlled according to a predetermined treatment plan and electrical control instructions, so that the patient's lesion may be located at a center of a radiation focus, thereby performing a fixed-point radiation therapy on the patient's lesion.

During each radiation therapy, an inner cavity of a collimating body in the radiotherapy device is an irradiation therapy cavity. By controlling the movement of the three-dimensional therapy couch to change different positions (i.e., automatic positioning), a multi-target radiation therapy may be achieved, and a positioning accuracy of targets may be improved, so as to reduce the auxiliary time of therapy.

However, when the patient's lesion is located in a relatively remote position, due to errors in calculation of the planned therapy space or in a motion control system of the three-dimensional therapy couch, an actual motion trajectory of the three-dimensional therapy couch easily exceeds a space of the irradiation therapy cavity, which causes the head frame positioning apparatus used for fixing the patient's head to mistakenly collide with an inner cavity wall of the collimating body to result in an unwanted injuries to the patient.

Figure 4:
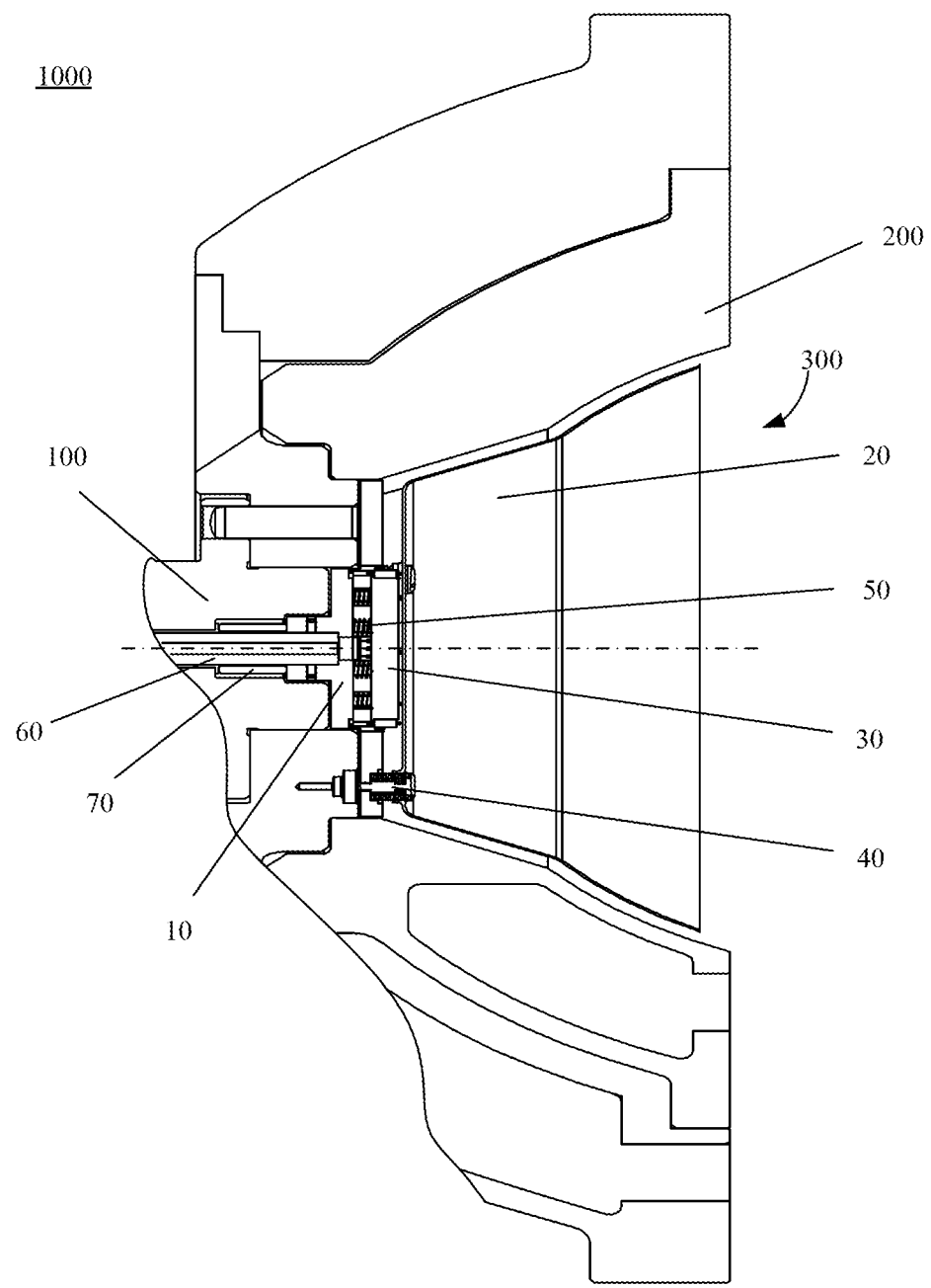
FIG. 4 is a schematic partial sectional view of a radiotherapy device, in accordance with some embodiments of the present disclosure.

Referring to FIGS. 1 and 4, some embodiments of the present disclosure provide an anti-collision apparatus 300 applied to a radiotherapy device 1000. The radiotherapy device 1000 includes: a device body 100, a collimating body 200 and the anti-collision apparatus 300. The collimating body 200 is rotatably connected to the device body 100. The anti-collision apparatus 300 is located inside the collimating body 200 and is fixedly connected to the device body 100.

Structures of the device body 100 and the collimating body 200 may be selectively set according to actual requirements, which are not limited in the embodiments of the present disclosure.

The anti-collision apparatus 300 includes an anti-collision cover 20 and a detection component 30. The detection component 30 is disposed outside a bottom end of the anti-collision cover 20 along an axial direction (the X-X' direction in FIG. 1) of the anti-collision cover 20. An axial gap (e.g., the gap along the X-X' direction in FIG. 1) is provided between the detection component 30 and the anti-collision cover 20. The axial gap is relatively small, and thus is not shown in the figure.

The anti-collision cover 20 is located inside the collimating body 200 of the radiotherapy device 1000, and a contour shape of the anti-collision cover 20 is matched with a shape of a cavity of the collimating body 200. The anti-collision cover 20 is arranged coaxially with the collimating body 200. The collimating body 200 is rotatably connected to the device body 100, and an axis of the collimating body 200 is a center line of rotation of the collimating body 200.

In the embodiments of the present disclosure, the detection component 30 is disposed outside the bottom end of the anti-collision cover 20 along the axial direction of the anti-collision cover 20, which may avoid reserving a mounting space for the detection component 30 between the anti-collision cover 20 and the collimating body 200 along a radial direction (e.g., the Y-Y' direction in FIG. 1), so that a radial gap between the anti-collision cover 20 and the collimating body 200 may be moderately reduced to avoid reducing the space in the limited therapy cavity due to the mounting of the detection component 30.

The detection component 30 is configured to collect a trigger signal, and output a collision signal according to the trigger signal. The trigger signal includes a mechanical trigger signal or an electromagnetic trigger signal generated when the axial gap between the detection component 30 and the anti-collision cover 20 is reduced to a target value.

Here, the axial gap between the detection component 30 and the anti-collision cover 20 is reduced means that the anti-collision cover 20 is displaced towards the detection component 30 along the axial direction under action of an external force. For example, in a case where the anti-collision cover 20 collides with the patient or the head frame positioning device for the patient, the anti-collision cover 20 deforms or moves to a side where the detection component 30 is located under the action of the external force. In this way, when the axial gap between the detection component 30 and the anti-collision cover 20 is reduced to the target value, the detection component 30 may collect a trigger signal caused by the reduction of the axial gap to the target value and output a collision signal according to the trigger signal, so that the rotation of the collimating body 200 is controlled, thereby avoiding the collision between the anti-collision cover 20 and the collimating body 200, or timely stopping the rotation of the collimating body 200 at the beginning of the collision between the anti-collision cover 20 and the collimating body 200. The target value may be selectively set according to actual requirements, which is not limited in the embodiments of the present disclosure.

With continued referring to FIGS. 1 and 4, in some embodiments, the anti-collision apparatus 300 further includes a fixing base 10 and a first elastic component 40. The fixing base 10 is located on a side of the detection component 30 away from the anti-collision cover 20. The first elastic component 40 is connected to the fixing base 10 and the anti-collision cover 20. The first elastic component 40 is configured to buffer a first collision force of the anti-collision cover 20 (i.e., a force to which the anti-collision cover 20 is subject due to its collision with a foreign object) and to reset the anti-collision cover 20. The anti-collision cover 20 is fixed to the device body 100 of the radiotherapy device 1000 through the fixing base 10. In this way, when the collimating body 200 rotates, the anti-collision cover 20 and the device body 100 remain relatively stationary.

In some embodiments of the present disclosure, the anti-collision cover 20 is connected to the fixing base 10 through the first elastic component 40. In this way, at the beginning when the anti-collision cover 20 is subject to the first collision force, the first collision force suffered by the anti-collision cover 20 is buffered by the first elastic component 40, which may not only protect the anti-collision cover 20, but also gain more time for corresponding control response of the collimating body 200, thereby avoiding a serious collision between the anti-collision cover 20 and the collimating body 200, and further effectively reducing safety risks of the patient during the radiation therapy. Of course, the use of the first elastic component 40 may also ensures that the anti-collision cover 20 is reset after the first collision force is eliminated. That is, the anti-collision cover 20 is rebounded to an initial position before being subject to the force, thereby facilitating a next use of the anti-collision apparatus.

Figure 2:
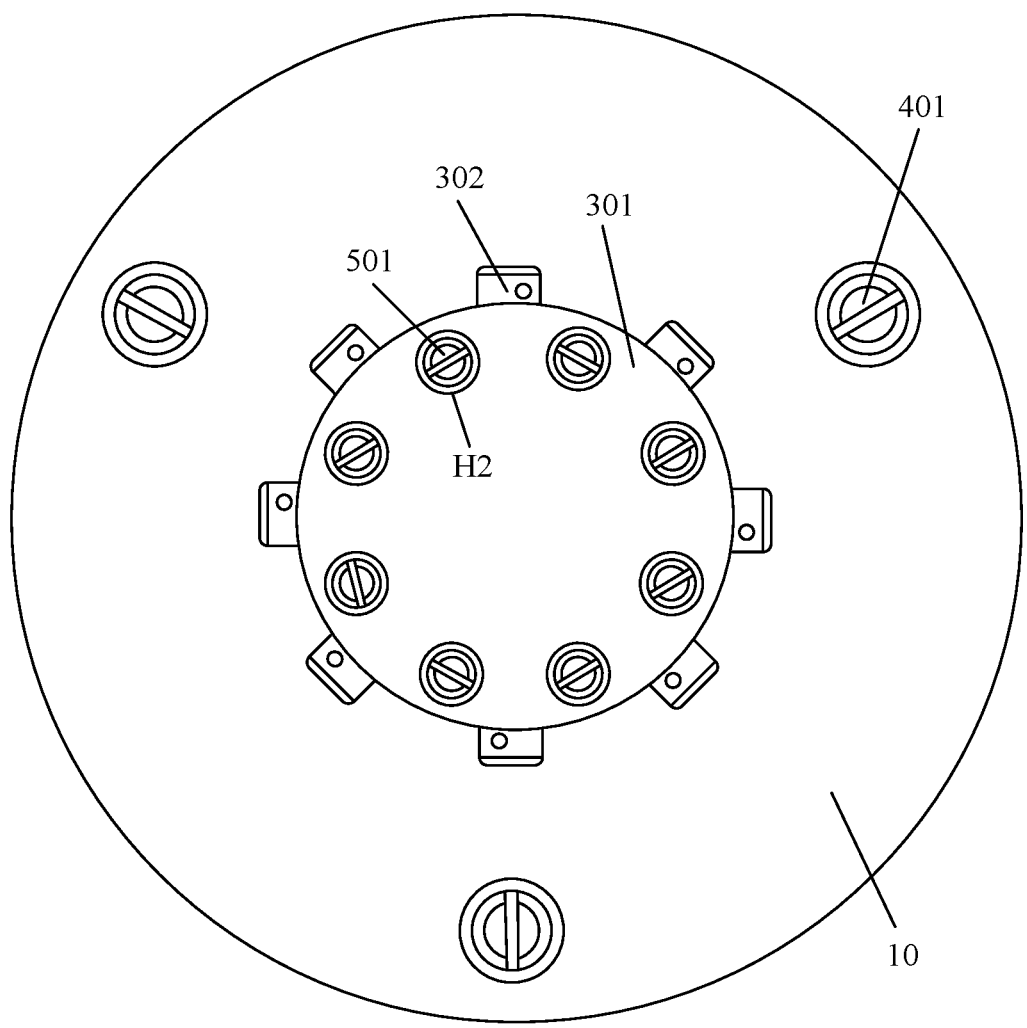
FIG. 2 is a schematic partial side view of an anti-collision apparatus, in accordance with some embodiments of the present disclosure.

In some embodiments, with continued referring to FIGS. 1 and 2, the detection component 30 includes a switch panel 301, and a plurality of detection switches 302 uniformly distributed on a circumferential side of the switch panel 301. In some embodiments of the present disclosure, the plurality of detection switches 302 are uniformly provided on the circumferential side of the switch panel 301, so that the plurality of detection switches 302 may be triggered in a case where the axial gaps between the anti-collision cover 20 and the plurality of detection switches 302 are reduced to the target value, and thereby the plurality of detection switches 302 may output the collision signals to control the rotation of the collimating body 200.

In addition, the structure and the number of detection switches 302 may be set according to actual requirements. For example, the number of detection switches 302 is not less than four.

It will be supplemented that whether the trigger signal collected by the detection component 30 is a mechanical trigger signal or an electromagnetic trigger signal is related to a structure of the detection component 30.

In some examples, the detection switch 302 is a proximity switch, such as an electromagnetic proximity switch. The proximity switch is triggered if the proximity switch senses that the axial gap between the anti-collision cover 20 and the proximity switch is less than or equal to the target value when the anti-collision cover 20 approaches to the proximity switch. That is, an electromagnetic trigger signal is collected by the detection component 30.

In some other examples, the detection switch 302 is a microswitch, such as a mechanical microswitch; and a contact of the microswitch faces to the anti-collision cover 20. The micro switch is triggered when the contact of the sensitive switch is pressed by the anti-collision cover 20. That is, a mechanical trigger signal is collected by the detection component 30.

The collision signal is outputted by the detection component 30 according to the trigger signal generally in a form of an electrical signal. For example, the target value is set to 0.1 cm, and the electrical signal outputted by the detection component 30 may be 0 (low level) or 1 (high level).

In some examples, an collision signal of each detection switch 302 of the detection component 30 is a normally open signal, that is, each detection switch 302 is in an off-state when not triggered. In this case, the detection switches 302 are connected in parallel, which is correspond to a relation of logic "or". In this way, in a case where a distance between the anti-collision cover 20 and each detection switch 302 is greater than 0.1 cm, the detection switch 302 in the detection component 30 is not triggered and outputs an electrical signal 0 to maintain a control circuit of the collimating body 200 be in an on-state, so that the collimating body 200 is controlled to rotate normally. In a case where the distance between the anti-collision cover 20 and each detection switch 302 is less than or equal to 0.1 cm (including the distance between the anti-collision cover 20 and the detection switch 302 being 0 cm when the detection switch 302 is pressed by the anti-collision cover 20), any one of the detection switches 302 in the detection component 30 is triggered and outputs an electrical signal 1 to alarm that a collision has occurred or is about to occur, so that the control circuit of the collimating body 200 may be turned off to control the collimating body 200 to stop rotating.

In some other examples, the output signal of each detection switch 302 of the detection component 30 is a normally closed signal, that is, each detection switches 302 is in a closed state when not triggered. In this case, the detection switches 302 are connected in series, which is correspond to a relation of logic "and". In this way, in a case where the distance between the anti-collision cover 20 and each detection switch 302 is greater than 0.1 cm, the detection switch 302 in the detection component 30 is not triggered and outputs an electrical signal 1 to maintain the control circuit of the collimating body 200 be in an on-state, so that the collimating body 200 is controlled to rotate normally. In a case where the distance between the anti-collision cover 20 and each detection switch 302 is less than or equal to 0.1 cm (including the distance between the anti-collision cover 20 and the detection switch 302 being 0 cm when the detection switch 302 is pressed by the anti-collision cover 20), any one of the detection switches 302 in the detection component 30 is triggered and outputs an electrical signal 0 to alarm that a collision has occurred or is about to occur, so that the control circuit of the collimating body 200 may be turned off to control the collimating body 200 to stop rotating.

In some embodiments, with continue referring to FIG. 1, the anti-collision apparatus 300 further includes a second elastic component 50. The detection component 30 is connected to the fixing base 10 through the second elastic component 50. The second elastic component 50 is configured to buffer a second collision force of the anti-collision cover 20 (i.e., a force to which the anti-collision cover 20 is subject due to its collision with a foreign object) and to reset the detection component 30. The second collision force that can be buffered by the second elastic component 50 is less than the first collision force that can be buffered by the first elastic component 40. The second collision force is less than the first collision force. There are no special restrictions on the manner or structure of allowing the second collision force less than the first collision force, as long as these effects can be achieved.

Here, the second elastic component 50 and the first elastic component 40 have similar functions, and are both capable of buffering the collision force of the anti-collision cover 20. The differences between the second elastic component 50 and the first elastic component 40 lies in that arrangement positions are different and magnitudes of buffering forces are different. That is, the anti-collision apparatus 300 is provided with a two-stage buffer-reset structure. Since the second collision force that can be buffered by the second elastic component 50 is less than the first collision force that can be buffered by the first elastic component 40, at the beginning of a collision between the anti-collision cover 20 and the foreign object (e.g., the patient or the head frame positioning device for the patient), the second elastic component 50 is triggered preferentially to perform a first-stage buffering on the second collision force of the anti-collision cover 20. Then, in a case where a force of the foreign object to the anti-collision cover 20 is greater than the second collision force, the first elastic component 40 is continuously triggered to perform a second-stage buffering on the first collision force of the anti-collision cover 20.

Therefore, in some embodiments of the present disclosure, the first elastic component 40 and the second elastic component 50 are provided in the anti-collision apparatus, so that a force of the anti-collision cover 20 is buffered stage by stage when the anti-collision cover 20 is collided with the foreign object, thereby further gaining more time for the control response of the collimating body 200 to avoid a serious collision between the anti-collision cover 20 and the collimating body 200, and thus effectively improving the safety in use of the radiotherapy device, and further reducing the safety risks of the patient during the radiation therapy effectively.

The first elastic component 40 and the second elastic component 50 are configured to buffer the collision forces of the anti-collision cover 20, and their structures may be determined according to actual requirements, such as a force absorbed structure or an elastic structure that are capable of buffering the force.

In some embodiments, with continued referring to FIGS. 1 and 2, the first elastic component 40 includes at least three first axial screws 401 and a first spring 402 sleeved on each of the at least three first axial screws 401. The anti-collision cover 20 is provided with first through holes H1 in one-toone correspondence with the at least three first axial screws 401. Each first axial screw 401 is fixedly connected to the fixing base 10 by passing through a corresponding first through hole H1. Two ends of each first spring 402 are abutted against the fixing base 10 and the anti-collision cover 20, respectively.

The number and arrangement position of first through holes H1 in the anti-collision cover 20 are selectively set according to actual requirements. The number of first axial screws 401 corresponds to the number of first through holes H1. A structure of the first axial screws 401 is selectively set according to actual requirements. In some embodiments of the present disclosure, by using the at least three first axial screws 401, the anti-collision cover 20 can be supported in a stable plan before the anti-collision cover 20 is displaced by collision.

Optionally, a screw portion of the first axial screw 401 is of a stepped columnar structure with two thin ends and a thick middle portion. A thin end, away from the head, of the first axial screw 401 is provided with threads and is threadedly connected to the fixing base 10. A thin end, close to the head, of the first axial screw 401 is a polished rod, and a gap is provided between the thin end, close to the head, of the first axial screw 401 and the corresponding first through hole H1. A size of the gap is related to allowable safety movement margin of the anti-collision cover 20.

For example, a difference between a diameter of the first through hole H1 and a diameter of the thin end, close to the head, of the corresponding first axial screw 401 is greater than or equal to the allowable safety movement margin of the anti-collision cover 20. For example, the allowable safe movement margin of the anti-collision cover 20 is 5 mm. That is, the anti-collision cover 20 may move at most 5 mm along a radial direction of the first through hole H1 during a period from after the anti-collision cover 20 is collided with the foreign object to before the collimating body 200 stops rotating. In this way, the difference between the diameter of the first through hole H1 and the diameter of the thin end, close to the head, of the respective first axial screws 401 is greater than or equal to 5 mm, which may gain more time for the control response of the collimating body 200, thereby avoiding a serious collision between the anti-collision cover 20 and the collimating body 200.

On this basis, the two ends of the first spring 402 sleeved on each first axial screw 401 are abutted against the fixing base 10 and the anti-collision cover 20 respectively, so that the anti-collision cover 20 may follow the direction of its force to translate in an indefinite direction or swing in a small angle relative to the fixing base 10 during the period from after the foreign object collides with the anti-collision cover 20 to before the collimating body 200 stops rotating.

In some embodiments, with continued referring to FIGS. 1 and 2, the detection component 30 includes a switch panel 301 and a plurality of detection switches 302 uniformly distributed on a circumferential side of the switch panel 301. The second elastic component 50 includes at least three second axial screws 501 and a second spring 502 sleeved on each of the at least three second axial screws 501. The switch panel 301 is provided with second through holes H2 in one-to-one correspondence with the at least three second axial screws 501. Each second axial screw 501 is fixedly connected to the fixing base 10 by passing through a corresponding second through hole H2. Two ends of each second spring 502 are abutted against the fixing base 10 and the switch panel 301, respectively.

The number and arrangement position of second through holes H2 in the switch panel 301 are selectively set according to actual requirements. The number of second axial screws 501 corresponds to the number of second through holes H2. A structure of the second axial screws 501 may be determined according to actual requirements. In some embodiments of the present disclosure, by using the at least three second axial screws 501, the switch panel 301 can be supported in a stable plan before the switch panel 301 is displaced by collision.

Optionally, a screw portion of the second axial screw 501 is of stepped columnar structure with two thin ends and a thick middle portion. A thin end, away from the head, of the second axial screw 501 is provided with threads and is threadedly connected to the fixing base 10. A thin end, close to the head, of the second axial screw 501 is a polished rod, and there is a gap between the thin end, close to the head, of the second axial screw 501 and the corresponding second through hole H2.

The two ends of the second spring 502 sleeved on each second axial screw 501 are abutted against the fixing base 10 and the switch panel 301 respectively. In this way, the switch panel 301 is floatingly connected to the fixing base 10, that is, the switch panel 301 may translate in an indefinite direction or swing at a small angle relative to the fixing base 10.

In addition, in some of the above embodiments, a normal state of the first spring 402 and the second spring 502 which have been mounted are a compressed state. That is, the first spring 402 has an elastic effect on the fixing base 10 and the anti-collision cover 20 at both ends of the first spring 402, and the second spring 502 has an elastic effect on the fixing base 10 and the switch panel 301 at both ends of the second spring 502. An elastic force of each first spring 402 and an elastic force of each second spring 502 enable the anti-collision cover 20 and the switch panel 301 to rebound back to their positions before collision after being displaced by collision.

In a case where the detection switch 302 is a microswitch, the elastic force of the second spring 502 is slightly greater than a triggering force of the microswitch on the switch panel 301. The contact of the microswitch is compressed to its maximum stroke by the anti-collision cover 20 preferentially after the anti-collision cover 20 is collided with the foreign object. If the contact of the microswitch has been compressed to its maximum stroke, but the collision between the foreign object and the anti-collision cover 20 has not been released yet, the anti-collision cover 20 continues to compress the second spring 502, and the collision force of the anti-collision cover 20 is buffered by a compression margin of the second spring 502 (i.e., an effective stroke of the second spring 502 that may also be compressed), which may protect the microswitch and gain more time for the control response of the collimating body 200.

A compression margin of the first spring 402 is greater than or equal to a sum of the compression margin of the second spring 502 and the maximum stroke of the contact of the microswitch. In a case where the compression margin of the first spring 402 is greater than the sum of the compression margin of the second spring 502 and the maximum stroke of the contact of the micro switch, if no compression margin of the second spring 502 exists after the second spring 502 is compressed, but the collision between the foreign object and the anti-collision cover 20 has not been released yet, the anti-collision cover 20 may also continue to compress the first spring 402, and the collision force of the anti-collision cover 20 is buffered by the compression margin of the first spring 402. Therefore, the microswitch is protected further and gain more time for the control response of the collimating body 200 further.

It can be noted that the volume of the device body 100 of the radiotherapy device 1000 is relatively large and the structure is relatively complex. The entire structure of the radiotherapy device 1000 is not given in the drawings of the embodiments of the present disclosure and is only illustrated a partial structure thereof. Portions of the radiotherapy device 1000 that are not given in the drawings may be found in the relevant structures in the related art.

Figure 3:
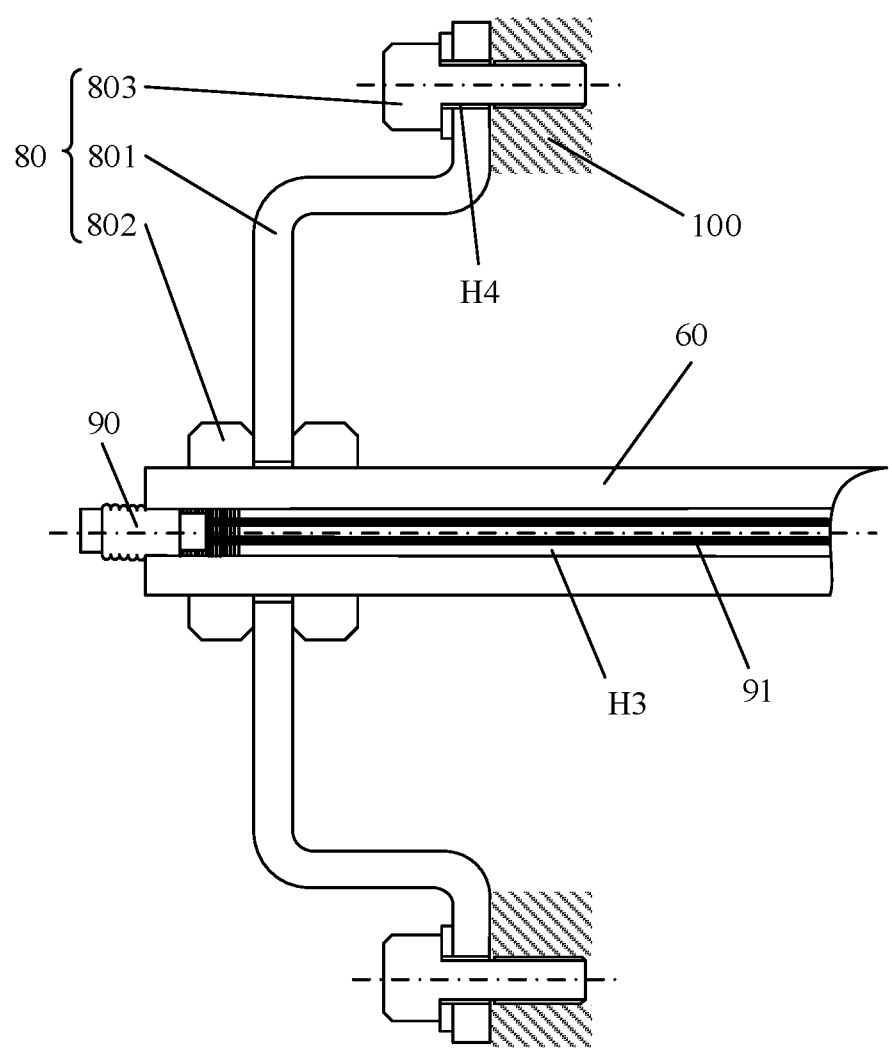
FIG. 3 is a schematic sectional view of an adjusting portion, in accordance with some embodiments of the present disclosure.

In some embodiments, referring to FIGS. 1 and 3, the anti-collision apparatus 300 further includes a fixing rod 60 connected to the fixing base 10. The fixing rod 60 is located on a side of the fixing base 10 away from the anti-collision cover 20. A length of the fixing rod 60 may be selectively set according to actual requirements. The fixing rod 60 is fixedly connected to the fixing base 10, for example, by a plurality of fastening screws 601 arranged along a radial direction of the fixing rod 60. The anti-collision apparatus 300 may be fixed to the device body 100 by the fixing base 10 and the fixing rod 60.

The device body 100 of the radiotherapy device 1000 is generally provided with a control system. The detection component 30 outputs the collision signal to the control system, and the control system may control the rotation of the collimating body 200 according to the collision signal. A structure and position of the control system may be selectively set according to actual requirements.

For example, the fixing rod 60 is of a hollow structure, and the fixing rod 60 includes a third through hole H3 arranged along the axial direction (e.g., the X-X' direction) thereof. The anti-collision apparatus 300 further includes at least one signal line 91 connected to the detection component 30, and the at least one signal line 91 is led out from the hollow portion of the fixing rod 60, i.e., led out through the third through hole H3.

The at least one signal line 91 is electrically connected to pins of the detection switches 302 in the detection component 30. In some examples, the detection switches 302 are connected in parallel, and the number of signal lines 91 is twice as much as the number of detection switches 302. In some other examples, the detection switches 302 are connected in series, the number of signal lines 91 is two, with less wiring and simple structure.

In some examples, referring to FIG. 3, the anti-collision apparatus 300 further includes a signal line plug 90. The signal line plug 90 is disposed on an end of the fixing rod 60 away from the fixing base 10, and is connected to the signal line 91.

Here, one end of the signal line plug 90 is connected to the signal line 91, and the other end of the signal line plug 90 is connected to the control system.

Optionally, the signal line plug 90 and the end of the fixing rod 60 are connected by a plug-in connection, for example, a threaded plug-in connection. In this way, it may ensure rapidity and convenience of the installation and maintenance of the signal line plug 90 and the signal line 91.

In some embodiments, referring to FIGS. 1 and 4, the anti-collision apparatus 300 further includes a spacer bush 70 sleeved on the fixing rod 60. The spacer bush 70 is in contact with an end face of the fixing base 10 away from the anti-collision cover 20, and is configured to be matched with the device body 100 to limit a distance between the fixing base 10 and the collimating body 200. Here, a size of the spacer bush 70 (e.g., a wall thickness, an outer wall diameter, an axial length, etc.) may be selectively set according to actual requirements.

The collimating body 200 is rotatably connected to the device body 100. Positions of the collimating body 200 and the device body 100 are fixed when the collimating body 200 is stationary relative to the device body 100. By using the spacer bush 70 to limit the gap between the fixing base 10 and the device body 100 in some embodiments of the present disclosure, it is ensured that sufficient gap is provided between the fixing base 10 and the collimating body 200, thereby avoiding interference between the fixing base 10 and the collimating body 200 in a case of relative movement, which is beneficial to improving the reliability of radiotherapy device.

In some embodiments, referring to FIG. 3, the anti-collision apparatus further includes an adjusting portion 80 sleeved on the fixing rod 60. The adjusting portion 80 is located on an end of the fixing rod 60 away from the fixing base 10, and is configured to be matched with the device body 100 to adjust a distance between the anti-collision cover 20 and the collimating body 200.

Here, the structure of the adjusting portion 80 may be selectively set according to actual requirements. For example, as shown in FIG. 3, the adjusting portion 80 includes a fixing frame 801, a lock nut 802 and a plurality of fastening bolts 803. The fixing frame 801 is sleeved on the fixing rod 60 and may move relative to the fixing rod 60. The lock nut 802 is used to lock and fix the fixing frame 801 and the fixing rod 60. At least two mounting holes H4 are provided in ends of the fixing frame 801 away from the fixing rod 60. The fastening bolt 803 passes through a corresponding mounting hole H4 to fix the fixing frame 801 to the device body 100 of the radiotherapy device 1000.

It can be understood that in some of the above embodiments, the first through hole H1, the second through hole H2, the third through hole H3 and the mounting hole H4 may be straight holes or stepped holes, etc., which is not limited in the present disclosure and may be selectively set according to actual requirements.

The contour of the anti-collision cover 20 is matched with the shape of the cavity of the collimating body 200, and central axes of the anti-collision cover 20 and the collimating body 200 are located in the same line. In some embodiments of the present disclosure, the distance between the anti-collision cover 20 and the collimating body 200 may be adjusted by the adjusting portion 80 sleeved on the fixing rod 60, thereby avoiding interference between the anti-collision cover 20 and the collimating body 200 in the case of relative movement, which is beneficial to improving the operational reliability of radiotherapy device.

It is worth mentioning that the anti-collision apparatus as described in some of the above embodiments exists as an independent apparatus, its components may be assembled and debugged offline, and then the anti-collision apparatus directly mounted on the device body 100 of the radiotherapy device. Therefore, the system integration and convenience of the radiotherapy device are improved, the assembly and maintenance time of the radiotherapy device may be greatly shortened, and the irradiation time of engineering service personnel in a radial state is reduced.

Referring to FIG. 4, some embodiments of the present disclosure provide a radiotherapy device. The radiotherapy device 1000 includes a device body 100, a collimating body 200 rotatably connected to the device body 100, and the anti-collision apparatus as described in some of the above embodiments. Beneficial effects that may be achieved by the radiotherapy device are the same as the beneficial effects that may be achieved by the anti-collision apparatus provided by some of the above embodiments, which will not be repeated herein.

In the above description of the embodiments, specific features, structures, materials or characteristics may be combined in any one or more embodiments or examples in a suitable manner.

The foregoing descriptions are merely some specific implementation manners of the present disclosure, but the protection scope of the present disclosure is not limited thereto, and changes or replacements that any person skilled in the art could readily conceive of within the technical scope of the present disclosure shall be included in the protection scope of the present disclosure. Therefore, the protection scope of the present disclosure shall be subject to the protection scope of the claims.

What is claimed is:

1. An anti-collision apparatus, comprising:
    an anti-collision cover;
    a detection component including a switch panel and a plurality of detection switches uniformly distributed on a circumferential side of the switch panel, the detection component being disposed outside a bottom end of the anti-collision cover along an axial direction of the anti-collision cover, an axial gap being provided between the detection component and the anti-collision cover, wherein the detection component is configured to collect a trigger signal, and to output a collision signal according to the trigger signal; the trigger signal includes a mechanical trigger signal or an electromagnetic trigger signal generated when the axial gap is reduced to a target value;
    a fixing base located on a side of the detection component away from the anti-collision cover;
    a first elastic component disposed between and connected to the fixing base and the anti-collision cover, the first elastic component being configured to buffer a first collision force of the anti-collision cover and to reset the anti-collision cover; and
    a second elastic component disposed between and connected to the fixing base and the detection component, the second elastic component being configured to buffer a second collision force of the anti-collision cover and to reset the detection component, wherein the second elastic component is disposed between the fixing base and the switch panel; and the second collision force is less than the first collision force.

2. The anti-collision apparatus according to claim 1, wherein
    the first elastic component includes at least three first axial screws and a first spring sleeved on each of the at least three first axial screws;
    the anti-collision cover includes at least three first through holes; the at least three first through holes are in one-to-one correspondence with the at least three first axial screws;
    each first axial screw passes through a corresponding first through hole and is fixedly connected to the fixing base; and
    two ends of each first spring are abutted against the fixing base and the anti-collision cover, respectively.

3. The anti-collision apparatus according to claim 1, wherein
    the second elastic component includes at least three second axial screws and a second spring sleeved on each of the at least three second axial screws;
    the switch panel includes at least three second through holes; the at least three second through holes are in one-to-one correspondence with the at least three second axial screws;
    each second axial screw passes through a corresponding second through hole and is fixedly connected to the fixing base; and
    two ends of each second spring are abutted against the fixing base and the switch panel, respectively.

4. The anti-collision apparatus according to claim 3, wherein the detection switch is a proximity switch or a microswitch.

5. The anti-collision apparatus according to claim 1, further comprising:
    at least one signal line connected to the detection component; and
    a fixing rod connected to the fixing base and located on a side of the fixing base away from the anti-collision cover;
    wherein the fixing rod includes a third through hole arranged along an axial direction of the fixing rod, and the at least one signal line is led out through the third through hole.

6. The anti-collision apparatus according to claim 5, further comprising:
    a signal line plug disposed on an end of the fixing rod away from the fixing base and connected to the at least one signal line.

7. The anti-collision apparatus according to claim 5, further comprising a spacer bush sleeved on the fixing rod; and
    the spacer bush being in contact with an end face of the fixing base away from the anti-collision cover, and being configured to be matched with a device body to limit a distance between the fixing base and a collimating body.

8. The anti-collision apparatus according to claim 5, further comprising an adjusting portion sleeved on the fixing rod;
    the adjusting portion being located on an end of the fixing rod away from the fixing base, and being configured to be matched with a device body to adjust a distance between the anti-collision cover and a collimating body.

9. A radiotherapy device, comprising:
    a device body;
    a collimating body rotatably connected to the device body; and
    the anti-collision apparatus according to claim 1, the anti-collision apparatus being located inside the collimating body and fixedly connected to the device body.

10. The anti-collision apparatus according to claim 1, wherein the detection switch is a proximity switch or a microswitch.

11. The anti-collision apparatus according to claim 2, wherein a screw portion of the first axial screw is of a stepped columnar structure with two thin ends and a thick middle portion;
    a thin end of the first axial screw is provided with threads and is threadedly connected to the fixing base; and,
    another thin end of the first axial screw is a polished rod, and a gap is provided between the another thin end of the first axial screw and the corresponding first through hole.

12. The anti-collision apparatus according to claim 3, wherein a screw portion of the second axial screw is of a stepped columnar structure with two thin ends and a thick middle portion;

a thin end of the second axial screw is provided with threads and is threadedly connected to the fixing base; and, another thin end of the second axial screw is a polished rod, and a gap is provided between the another thin end of the second axial screw and the corresponding second through hole.

13. The anti-collision apparatus according to claim 8, wherein the adjusting portion includes a fixing frame, a lock nut and a plurality of fastening bolts;

the fixing frame is sleeved on the fixing rod and is capable of moving relative to the fixing rod;

the lock nut is used to lock and fix the fixing frame and the fixing rod;

at least two mounting holes are provided in ends of the fixing frame away from the fixing rod; and, a fastening bolt is configured to pass through a corresponding mounting hole to fix the fixing frame to a device body.

\* \* \* \* \*